(12) United States Patent
Hidaka et al.

(10) Patent No.: US 7,405,331 B2
(45) Date of Patent: Jul. 29, 2008

(54) HIGH-PURITY (FLUOROALKYL)BENZENE DERIVATIVE AND PROCESS FOR PRODUCING THE SAME

(75) Inventors: Toshio Hidaka, Ibaraki (JP); Norio Fushimi, Ibaraki (JP); Takafumi Yoshimura, Ibaraki (JP); Takeshi Kawai, Ibaraki (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 428 days.

(21) Appl. No.: 10/512,990

(22) PCT Filed: Apr. 24, 2003

(86) PCT No.: PCT/JP03/05261

§ 371 (c)(1),
(2), (4) Date: Jun. 16, 2005

(87) PCT Pub. No.: WO03/093212

PCT Pub. Date: Nov. 13, 2003

(65) Prior Publication Data

US 2006/0167324 A1 Jul. 27, 2006

(30) Foreign Application Priority Data

Apr. 30, 2002 (JP) .............................. 2002-128158

(51) Int. Cl.
*C07C 22/08* (2006.01)
(52) U.S. Cl. ..................... 570/145; 562/840; 562/857; 562/856
(58) Field of Classification Search ................. 570/145; 562/840, 857, 856
See application file for complete search history.

(56) References Cited

U.S. PATENT DOCUMENTS 3,966,832 A 6/1976 Lademann et al.

FOREIGN PATENT DOCUMENTS

| DE | 707 955 | 7/1941 |
|---|---|---|
| DE | 1 618 390 | 12/1970 |
| JP | 57-98224 | 6/1982 |
| JP | 57-98225 | 6/1982 |
| JP | 58-201732 | 11/1983 |

OTHER PUBLICATIONS

Supplementary European Search Report, for Application No. 03 72 3191, mailed Apr. 20, 2006.
W. H. Perkin, Jr. et al., "An Investigation of the Action of Halogens on 2:4-Dimethylbenzoyl Chloride", *Journal of the Chemical Society Transactions*, vol. 127, pp. 2275-2297(XP008062283), 1925.
W. Davies, et al., "The Cholrination and Bromination of the Toluic Acids and the Preparation of the Phthalaldehydic Acids", *Journal of the Chemical Society Transactions*, vol. 121, pp. 2202-2215, (XP008062282), 1922.

*Primary Examiner*—Elvis O Price
(74) *Attorney, Agent, or Firm*—Antonelli, Terry, Stout & Kraus, LLP.

(57) ABSTRACT

The process for producing a (fluoroalkyl)benzene derivative according to the present invention comprises a step of reducing the total content of group 3 to group 12 transition metals in an alkylbenzene derivative to 500 ppm or less in terms of metal atoms; a step of halogenating the branched alkyl group of the purified alkylbenzene derivative by a photohalogenation to obtain a (haloalkyl)benzene derivative; and a step of subjecting the (haloalkyl)benzene derivative to a halogen-fluorine exchange using HF in an amount of 10 mol or higher per one mole of the (haloalkyl)benzene derivative. The (fluoroalkyl)benzene derivative produced by the process is reduced in the content of impurities such as residual halogens and residual metals, and is useful as intermediates for functional chemical products for use in applications such as medicines and electronic materials.

10 Claims, No Drawings

HIGH-PURITY (FLUOROALKYL)BENZENE DERIVATIVE AND PROCESS FOR PRODUCING THE SAME

This application is a 371 of PCT/JP03/05261, filed Apr. 24, 2003, which claims benefit to foreign application JP 2002-128158, filed Apr. 30, 2002.

TECHNICAL FIELD

The present invention relates to (fluoroalkyl)benzene derivatives and a process for producing the same. More particularly, the invention relates to impurity-reduced, high-purity (fluoroalkyl)benzenecarboxylic acid derivatives, especially 3,5-bis(trifluoromethyl)benzoic acid and derivatives thereof, which are useful in the fields of medicines, electronic materials, etc., and a process for producing the same. The high-purity (fluoroalkyl)benzenecarboxylic acid derivatives are useful as intermediate materials for the production of medicines, electronic materials such as photoresists, and functional chemical products.

BACKGROUND ARTS

In recent years, fluorine-containing compounds have been noticed in various fields of applications such as medicines and electronic materials because of peculiar properties thereof, and have been used in numerous application fields by utilizing their functions attributable to fluorine atoms. Therefore, various methods for effectively introducing fluorine atoms into compounds have been studied. Conventionally known fluorination techniques include, for example, a direct fluorination method using a fluorine gas, a so-called halogen exchange method in which a compound containing a halogen atom such as chlorine and bromine is reacted with HF or KF to replace the halogen atom with fluorine, a method using a combination of hydrogen fluoride with a base such as pyridine and triethylamine, a method using a hypervalent iodine, e.g., $IF_5$, an electrolytic fluorination method, etc. In the present invention, the "halogen" means halogens other than fluorine unless otherwise specified.

Among these methods, the halogen-fluorine exchange method has been extensively used because fluorine atoms can be introduced relatively easily and aimed fluorine-containing compounds can be produced easily, although the use of halogen compounds as the starting materials is somewhat undesirable. The details about the techniques for producing fluorine compounds by the halogen-fluorine exchange method are described, for example, in Adv. Fluorine Chem., 1963, (3), p. 181. This document describes the halogen-fluorine exchange reaction between halogen-containing aliphatic compounds, aromatic compounds, branched aromatic compounds, heterocyclic compounds, carboxylic acids, sulfonic acids, silicon compounds or phosphorus compounds with fluorine compounds such as HF, KF, $SbF_3$ and $SbF_5$.

The halogen-fluorine exchange reaction requires a halogenated precursor corresponding to the aimed compound. There are also many well known techniques for introducing halogens to produce such a halogenated precursor, for example, a method using chlorine gas, iron chloride, phosphorus trichloride, phosphorus pentachloride, thionyl chloride, sulfuryl chloride, aluminum chloride, chloroform, carbon tetrachloride, titanium chloride, phosgene, N-chlorosuccinimide, etc.; and a method using zeolites such as zeolite X, Y, L and β and mordenite together with chlorine gas, thionyl chloride, sulfuryl chloride or the like for improving selectivity of the halogenation.

In the photochlorination using chlorine gas under irradiation of light, even low-reactive molecules such as methane are effectively converted into methyl chloride by a free-radical chain reaction. This method is useful for chlorinating side chains of aliphatic or aromatic compounds. For example, Kirk-Othmer, "Encyclopedia of Chemical Technology", 4th edition, describes the production of benzyl chloride from toluene as an example of the photochlorination of side chain of aromatic compounds.

Not Limited merely to aliphatic or aromatic hydrocarbons, the photohalogenation is widely applied to various compounds such as heterocyclic compounds, carboxylic acids, sulfonic acids, silicon compounds and phosphorus-containing compounds.

For example, JP 2001-294551 A discloses a method for producing 3,5-bis(trichloromethyl)benzoyl chlorides by the photochlorination of 3,5-dimethylbenzoyl chlorides.

This method has been also disclosed in French Patent No. 820696 (1937). The French Patent teaches a method for chlorinating branched methyl group of methyl-containing benzenecarboxylic acids by chlorine gas, and describes in Example 10 an actual procedure for producing 3,5-bis(trichloromethyl)benzoyl chloride from 3,5-dimethylbenzoyl chloride by introducing chlorine atom under irradiation of light. Further, U.S. Pat. No. 2,181,554 (1939) discloses a method for producing 3,5-bis(trifluoromethyl)benzoyl fluoride from 3,5-bis(trichloromethyl)benzoyl chloride by the halogen exchange. Concerning the photohalogenation, there are so many other documents to make it difficult to comprehensively review them.

The above known photohalogenation methods and halogen-fluorine exchange methods are extensively used for introducing fluorine atoms to various compounds. Since these methods use a halogenated compound as a precursor for introducing fluorine atoms, the final products inevitably contain halogens as impurities. The impurities such as residual halogens, residual metals and residual alkali or alkaline earth metals generally affect adversely in the application fields of medicine and electronic materials, and should be reduced to a ppb level or less in some cases. The residual halogens, for example, in medical applications pyrogen or other trace impurities tend to significantly affect human health and in electronic material applications such as photoresists the residual chlorine causes corrosion of electronic devices. The residual metals, for example, residual Pd migrates to cause defective insulation or defective operation. Sb remaining in chemically-amplified positive photoresists causes a positive-negative reversal during the irradiation of X-ray or electron beams. U, Th, etc., remaining in sealing materials cause soft error. Thus, the residual impurity elements have adverse influences in many cases. Therefore, it has been strongly required to minimize the content of impurities such as residual halogens and residual metals.

DISCLOSURE OF THE INVENTION

An object of the present invention is to provide (fluoroalkyl)benzene derivatives having their contents of impurities such as residual halogens and residual metals reduced which are useful as intermediates for the production of functional chemical products such as medicines and electronic materials, and a simple process for producing the (fluoroalkyl)benzene derivatives by photohalogenation and halogen-fluorine exchange.

As a result of extensive research for solving the above problems in the process for producing (fluoroalkyl)benzene derivatives by subjecting industrially readily available alkylbenzene derivatives to photohalogenation and then halogen-fluorine exchange, the inventors have found that the residual amount of impurity halogens and impurity elements can be drastically reduced by conducting the photohalogenation after reducing the content of transition metals in the alkylbenzene derivatives to a limited value or less and then allowing the halogen-fluorine exchange using HF to proceed sufficiently under specific conditions, and if required, by optionally combining a purification step such as crystallization, distillation and thermal contact with hydrocarbons. The invention has been accomplished on the basis of this finding.

Thus, the invention provides a process for producing a high-purity (fluoroalkyl)benzene derivative comprising:

a step of subjecting an alkylbenzene derivative to a photohalogenation using a halogen except for fluorine to halogenate at least one alkyl, thereby producing a (haloalkyl)benzene derivative, the alkylbenzene derivative being represented by the formula (1):

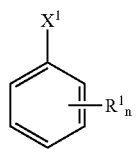

(1)

wherein $X^1$ is hydrogen, hydroxyl, alkyl, aryl, halogen inclusive of fluorine, formyl, carboxyl, nitro, cyano, amino, hydroxymethyl, aminomethyl, carbamoyl, sulfonic acid group or halogenocarbonyl inclusive of fluorocarbonyl, or $X^1$ is alkyloxycarbonyl, alkylcarbonyl, arylcarbonyl, alkyloxy or aryloxy, each being optionally substitute; $R^1$ is carboxyl, halogenocarbonyl inclusive of fluorocarbonyl, alkyloxycarbonyl, aryloxycarbonyl, substituted or unsubstituted alkyl, or substituted or unsubstituted aryl; n is an integer of 1 to 5 with the proviso that when n is 2 to 5, a plurality of $R^1$ groups may be the same or different, but at least one of $R^1$ is alkyl; and a step of subjecting the (haloalkyl)benzene derivative to a halogen-fluorine exchange using HF to produce the (fluoroalkyl)benzene derivative represented by the formula (2):

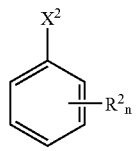

(2)

wherein $X^2$ corresponds to $X^1$ of a formula (1) and is hydrogen, hydroxyl, fluoroalkyl, aryl, halogen inclusive of fluorine, formyl, fluorocarbonyl, nitro, cyano, amino, hydroxyfluoromethyl, aminofluoromethyl, carbamoyl or sulfonylfluoride, or $X^1$ is fluoroalkyloxycarbonyl, fluoroalkylcarbonyl, arylcarbonyl, fluoroalkyloxy or aryloxy, each being optionally substituted; $R^2$ corresponds to $R^1$ of the formula (1) and is fluorocarbonyl, fluoroalkyloxycarbonyl, aryloxycarbonyl, substituted or unsubstituted fluoroalkyl, or substituted or unsubstituted aryl; n is as defined above, with the proviso that when n is 2 to 5, a plurality of $R^2$ groups may be the same or different, but at least one of $R^2$ is fluoroalkyl, wherein a total content of group 3 to group 12 transition metals in the alkylbenzene derivative is reduced to 500 ppm or less in terms of atomic basis; and 10 mol or more HF is used per one mole of the (haloalkyl)benzene derivative.

PREFERRED EMBODIMENT TO CARRY OUT THE INVENTION

The alkylbenzene derivatives represented by the formula (1) which are used in the first step for the side chain halogenation (except for fluorination) in the invention have at least one branched alkyl group which can be halogenated and may further have a plurality of substituent groups other than the branched alkyl groups.

The alkylbenzene derivatives used as the starting materials in the invention are represented by the following formula (1):

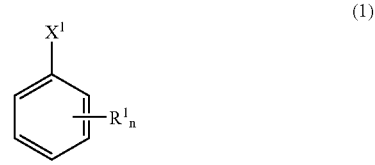

(1)

In the formula (1), $X^1$ represents hydrogen, hydroxyl, alkyl preferably $C_1$ to $C_{24}$ alkyl, aryl such as phenyl, halogen inclusive of fluorine, formyl, carboxyl, nitro, amino, hydroxymethyl, aminomethyl, carbamoyl, sulfonic acid group, or halogenocarbonyl inclusive of fluorocarbonyl. $X^1$ also represents alkyloxycarbonyl preferably ($C_1$ to $C_8$ alkyl)oxycarbonyl, alkylcarbonyl preferably ($C_1$ to $C_8$ alkyl)carbonyl, alkylcarbonyl, alkyloxy preferably ($C_1$ to $C_8$ alkyl)oxy, or aryloxy, each being optionally substituted. Examples of the substituent groups for alkylcarbonyl, arylcarbonyl, alkyloxy or aryloxy include halogens inclusive of fluorine, hydroxyl, alkyl and alkyloxy. Preferred $X^1$ are carboxyl, cyano, hydroxyl, formyl and amino.

$R^1$ represents carboxyl, halogenocarbonyl inclusive of fluorocarbonyl, alkyloxycarbonyl preferably ($C_1$ to $C_8$ alkyl)oxycarbonyl, aryloxycarbonyl, substituted or unsubstituted alkyl preferably $C_1$ to $C_8$ alkyl, or substituted or unsubstituted aryl, with the proviso that at least one of $R^1$ is alkyl. Examples of the substituent groups for alkyl or aryl include methyl, ethyl, propyl, isopropyl, phenyl and methylphenyl. Preferred $R^1$ are methyl, ethyl, propyl and isopropyl.

Specific examples of the alkylbenzene derivatives include alkylbenzaldehydes such as 4-methylbenzaldehyde, 4-ethylbenzaldehyde, 2,4-dimethylbenzaldehyde, 2,5-dimethylbenzaldehyde, 3,4-dimethylbenzaldehyde, 3,5-dimethylbenzaldehyde, 2,4,5-trimethylbenzaldehyde, 2,4,6-trimethylbenzaldehyde, 4-isopropylbenzaldehyde, 4-isobutylbenzaldehyde, 4-methylbiphenylaldehyde, 4-ethylbiphenylaldehyde, 4-n-propylbiphenylaldehyde, 4-n-butylbiphenylaldehyde and methyltetralinaldehyde; benzenecarboxylic acids such as 2-methylbenzoic acid, 3-methylbenzoic acid, 4-methylbenzoic acid, 4-ethylbenzoic acid, 2,4-dimethylbenzoic acid, 2,5-dimethylbenzoic acid, 3,4-dimethylbenzoic acid, 3,5-dimethylbenzoic acid, 2,4,5-trimethylbenzoic acid, 2,4,6-trimethylbenzoic acid, 4-isopropylbenzoic acid, 4-isobutylbenzoic acid, 4-methylbiphenylcarboxylic acid, 4-ethylbiphenylcarboxylic acid, 4-n-propylbiphenylcarboxylic acid, 4-n-butylbiphenlcarboxylic acid and methyltetralincarboxylic acid; acid halides derived from the above benzenecarboxylic acids; alkylphenols such as 2,4-dimethylphenol, 2,5-dimethylphenol, 3,4-dimethylphenol and 3,5-dimethylphenol; other compounds such as 3,5-dimethylhalogenobenzenes, 4-chloro-3,5-dimethlylphenol, N,N-diethyl-m-toluamide, 2,4-dimethylbenzenesulfonic acid and dixylylmethane; and position isomers of the above compounds.

The total content of group 3 to group 12 transition metals in the alkylbenzene derivative (hereinafter refer to as "transition metal content") is 500 ppm or less and preferable 100 ppm or less in terms of atomic basis. In particular, the content of Fe is preferably 50 ppm or less. When the transition metal content is more than 500 ppm, in addition to the aimed side chain halogenation, side reactions such as nucleus halogenation to aromatic ring tend to occur. By-products produced increase the residual halogen impurities in the final products. If the transition metal content in the starting material is more than 500 ppm, the starting material is used after reducing the transition metal content to 500 ppm or less by distillation or adsorption treatment with activated carbon, silica gel, alumina, activated clay, ion-exchange resin, etc. The transition metal content can be reduced to 10 ppm or less industrially.

The side chain halogenation in the invention is preferably conducted by a photohalogenation method, although known techniques such as a method of using chlorine gas, bromine gas, iron chloride, phosphorus trichloride, phosphorus pentachloride, thionyl chloride, sulfuryl chloride, aluminum chloride, chloroform carbon tetrachloride, titanium tetrachloride, phosgene and N-chlorosuccinimide, and a method using zeolites such as zeolites X, Y, L and β, and mordenite together with chlorine gas, thionyl chloride, sulfuryl chloride, etc. can be applicable. The photohalogenation of side chains of aromatic compounds is widely used in industrial process and uses chlorine, bromine and iodine as the halogen source, with chlorine being preferred because of its low costs. The halogens to be used are not particularly restricted as long as they are industrially available, and preferably dried so as to have a water content of 100 ppm or less. Although not critical, the supplying amount of the halogen is preferably 50 to 3,000 parts by weight based on 100 parts by weight of the alkylbenzene derivative, and the supplying rate is preferably 0.1 g/min or more. Chlorine may be usually supplied to a reaction solution in a gaseous state by bubbling. Bromine or iodine are supplied to a reaction solution in a liquid or solid state. The halogenation is performed under a pressure of 0.06 to 0.5 MPa, usually under atmospheric pressure. The temperature for halogenation is 50 to 250° C. and preferably 80 to 200° C. When the temperature reaches a predetermined temperature, the supply of halogen is started to initiate the reaction. The reaction time is preferably 0.5 to 24 h.

The halogenation of the side chains of the alkylbenzene derivative is conducted under the exposure to light. The source of light is not particularly restricted. In industrial process, a high reactivity and a high selectivity to the side chain halogenation can be obtained by disposing a source of light such as a mercury lamp and a tungsten lamp to a reactor. In place of exposure to light, the use of a radical generator such as benzoyl peroxide and 2,2-azobis(isobutylonitrile) is effective to enhance the reactivity. An amount as small as 0.001 to 0.01 part by weight of the radical generator based on one part by weight of the starting alkylbenzene derivative is sufficient for the purpose. The radical generator may be effectively used under exposure to light without causing any problems.

If the starting alkylbenzene derivative is liquid under the conditions for the side chain halogenation, the use of a solvent is not necessarily required. However, solvents inert to the halogenation such as o-dichlorobenzene, chlorobenzene, carbon tetrachloride and benzonitrile may be used to facilitate handling of the starting material. The amount of the solvent to be used is preferably 0.5 to 100 parts by weight and more preferably 1 to 50 parts by weight based on one part by weight of the starting alkylbenzene derivative.

By the first step of side chain halogenation of the invention, a corresponding (haloalkyl)benzene derivative is obtained. Examples thereof include (haloalkyl)benzenecarboxylic acids such as 2-(tri-halomethyl)benzoic acids, 3-(trihalomethyl)benzoic acids, 4-(trihalomethyl)benzoic acids, 4-(trihaloethyl)benzoic acids, 4-(pentahaloethyl)benzoic acids, 2,4-bis(trihalomethyl)benzoic acids, 2,5-bis(trihalomethyl) benzoic acids, 3,4-bis(trihalomethyl)benzoic acids, 3,5-bis (trihalomethyl)benzoic acids, 2,4,5-tris(trihalomethyl) benzoic acids, 2,4,6-tris(trihalomethyl)benzoic acids, 4-(trihaloisopropyl) benzoic acids, 4-(hexahaloisopropyl) benzoic acids, 4-(trihaloisobutyl)benzoic acids, 4-(hexahaloisobutyl)benzoic acids, 4-(trihalomethyl)biphenylcarboxylic acids, 4-(pentahaloethyl)biphenylcarboxylic acids, 4-(hexahalo-n-propyl)biphenylcarbocylic acids, 4-(hexahalo-n-butyl)biphenylcarboxylic acids and (trihalomethyl) tetralincarboxylic acids; acid halides of these acids; and (haloalkyl)phenols such as 2,4-bis(trihalomethyl)phenols, 2,5-bis(trihalomethylphenols, 3,4-bis(trihalomethyl)phenols and 3,5-bis(trihalomethyl)phenols. The obtained (haloalkyl)benzene derivative may be directly used in the subsequent step, but are preferably subjected to known purification treatments such as distillation and crystallization to minimize the content of impurities.

The second step of the invention is the halogen-fluorine exchange in which the (haloalkyl)benzene derivative obtained in the first step is converted into a corresponding (fluoroalkyl)benzene derivative. The halogen-fluorine exchange may be performed, for example, by a known method described in Adv. Fluorine Chem., 1963, (3), 181.

HF is preferably used in the halogen-fluorine exchange, optionally together with on acid having a Hammett acidity function $H_0$ of −10 or less such as $ClSO_3H$, $FSO_3H$ and $CF_3SO_3H$ or a Lewis acid such as $BF_3$, $SbF_5$ and $TaF_5$. These acids or Lewis acids malt be used in an amount of 0.001 to 0.1 mol per one mole of HF. Generally, HF is introduced into a pressure reactor together with the (haloalkyl)benzene derivative for the reaction. Alternatively, HF may be introduced into a reactor after the reactor containing the (haloalkyl)benzene derivative is hearted to a desired temperature. Since HCl is generated with the progress of the reaction, it is preferred to prevent the increase in the inner pressure of the system by a suitable method such as exhaustion through a back-pressure valve.

HF is used in an amount of 10 to 500 mol and preferably 20 to 200 mol per one mole of the (haloalkyl)benzene derivative as a substrate. When less than 10 mol, the halogen-fluorine exchange does not proceed sufficiently, thereby not only failing to produce the aimed (fluoroalkyl)benzene derivative at a high yield, but also causing a large amount of halogen compounds to remain as impurities in the product.

Although the halogen-fluorine exchange proceeds at room temperature, it is preferred to adequately select the reaction temperature from the range of 20 to 400° C. depending upon the kind of (haloalkyl)benzene derivative to allow the reaction to proceed sufficiently. For example, the halogen-fluorine exchange of the (haloalkyl)benzenecarboxylic acids is usually performed at 100° C. or higher, preferably 150 to 200° C. for 0.1 to 20 h, while preferably performed at 20 to 100° C. for 0.1 to 20 h in case of the (haloalkyl)phenols.

Examples of the (fluoroalkyl) benzene derivatives obtained by the halogen-fluorine exchange include (fluoroalkyl)benzenecarboxylic acids such as 2-(trifluoromethyl)benzoic acid, 3-(trifluoromethyl)benzoic acid, 4-(trifluoromethyl) benzoic acid, 4-(trifluoroethyl)benzoic acid, 4-(pentafluoroethyl)benzoic acid, 2,4-bis(trifluoromethyl)benzoic acid, 2,5-bis(trifluoromethyl)benzoic acid, 3,4-bis(trifluoromethyl)benzoic acid, 3,5-bis(trifluoromethyl)benzoic acid, 2,4,5-tris(trifluoromethyl)benzoic acid, 2,4,6-tris(trifluoromethyl)benzoic acid, 4-(trifluoroisopropyl)benzoic acid, 4-(hexafluoroisopropyl)benzoic acid, 4-(trifluoroisobutyl)benzoic acid, 4-(hexafluoroisobutyl)benzoic acid, 4(trifluoromethyl)biphenylcarboxylic acid, 4-(trifluoroethyl)biphenylcarboxylic acid, 4-(pentafluoroethyl)biphenylcarboxylic acid, 4-(trifluoro-n-propyl)biphenylcarboxylic acid, 4-(hexafluoro-n-propyl)biphenylcarboxylic acid, 4-(n-trifluorobutyl)biphenylcarboxylic acid, 4-(n-hexafluorobutyl) biphenylcarboxylic acid and (trifluoromethyl)tetralincarboxylic acid; acid fluorides of these acids; and (fluoroalkyl) phenols such as 2,4-bis(trifluoromethyl)phenol, 2,5-bis (trifluoromethyl)phenol, 3,4-bis(trifluoromethyl)phenol and 3,5-bis(trifluoromethyl)phenol.

By carrying out the first and second steps under the conditions mentioned above, the content of halogen impurities (halogens other than fluorine in the (fluoroalkyl)benzene derivatives) in the (fluoroalkyl)benzene derivatives produced in the second step is reduced to 1% by weight or less and preferably 0.5% (by weight or less in terms of halogen atoms, and the content of metal impurities is reduced to 100 ppm or less and preferably 50 ppm or less in terms of metal atoms.

When the product of the halogen-fluorine exchange is a (fluoroalkyl)benzenecarboxylic acid fluoride, the impurities therein is further reduced by suitably combining distillation, sublimation, crystallization, etc. after removing excess HF and HCl remaining after the halogen-fluorine exchange. The method for removal of the excess HF and residual HCl is not particularly restricted. For example, the excess HF and residual HCl are removed at room temperature or by slightly heating in a halogen-fluorine exchange reactor. By introducing an inert gas such as nitrogen gas into the reaction system, the removal is accelerated. This operation may be performed either under atmospheric pressure or reduced pressure.

Also, the reaction product solution may be supplied to a distillation column under reflux of an organic solvent, where HF and HCl are vaporized by the heat of solvent vapor and separated form the product by gas-liquid separation. The reaction product moves into the bottom of the distillation column, and the vaporized HF and HCl pass through a reflux condenser and separated in a downstream condenser. The recovered liquid HF is reused. The solvent usable in thus procedure is preferably hydrocarbons that are capable of dissolving the reaction product and are inert thereto, with hexane, benzene, toluene, xylene, etc. being preferably used. The temperature and pressure for operating the procedure may be appropriately determined depending upon the solvent used.

After the above procedures, the reaction product, (fluoroalkyl)benzenecarboxylic acid fluoride, may be converted into various fluoroalkyl compounds directly or after further purified by distillation.

The fluoroalkyl compounds referred to herein may be (fluoroalkyl)benzenecarboxylic acids, (fluoroalkyl)benzenecarboxylic acid halides, (fluoroalkyl)benzenecarboxylic acid esters, (fluoroalkyl)benzaldehydes, (fluoroalkyl)benzonitriles, (fluoroalkyl)benzenecarboxyamides, etc. The fluoroalkyl compounds may be purified after reacting the (fluoroalkyl)benzene derivatives obtained by removing HF and HCl remaining after the halogen-fluorine exchange reaction with water, tetrahalogenosilicon, alcohol, ammonia, etc. Alternatively, a purified (fluoroalkyl)benzenecarboxylic acid fluoride obtained by the distillation of the reaction product mixture form the halogen-fluorine exchange is converted into the fluoroalkyl compound, which is then purified. The purification method includes distillation, crystallization, sublimation, etc. By any one of the methods or any combination thereof, the fluoroalkyl compounds reduced in impurities are obtained.

In case of producing the (fluoroalkyl)benzenecarboxylic acid, a crude product obtained by removing residual HF and HCl from the reaction solution after the halogen-fluorine exchange or a purified (fluoroalkyl)benzenecarboxylic acid fluoride obtained by distilling the crude product is reacted with water. The reaction proceeds merely by contacting with water, but may be conducted under heating. The use of a water-immiscible solvent such as ether which is capable of dissolving both the (fluoroalkyl)benzenecarboxylic acid fluoride and the (fluoroalkyl)benzenecarboxylic acid being produced is recommended because these compounds are easily separated from water. After completion of the reaction with water or removal of the solvent by distillation, the precipitated crude (fluoroalkyl)benzenecarboxylic acid may be purified by crystallization from a non-polar hydrocarbon organic solvent, for example, aliphatic hydrocarbons such as pentane, hexane and heptane, and aromatic hydrocarbons such as benzene, toluene and xylene, with hexane, benzene and toluene being preferred because of flexibility and easiness of recovery. These solvent may be used singly or in combination of two or more.

The crude (fluoroalkyl)benzenecarboxylic acid is dissolved in the solvent usually at 50 to 200° C. and preferably at a reflux temperature of the solvent for easiness of operation. The amount of the solvent to be used may be appropriately determined depending upon the kind of solvent, dissolving temperature, intended purity of the product, etc., and preferably, 1 to 50 times the crude (fluoroalkyl)benzenecarboxylic acid by weight. The solution prepared by dissolution under heating is immediately filtered while hot to remove impurities. After removal of the impurities, the decoloring treatment using activated carbon or adsorbent may be made, if required. The solution after removal of the impurities is then cooled to around room temperature or lower to precipitate crystals of the aimed compounds. The precipitated crystals are separated by a solid-liquid separation such as filtration and centrifugal separation which are generally used. The crystals as-separated have a much lower content of impurities, but may be further rinsed, if required. If a further removal of impurities is required, the above procedures are repeated until reaching the desired purity. The impurity-reduced (fluoroalkyl)benzenecarboxylic acids produced by the invention can be converted to (fluoroalkyl)benzyl alcohols by hydrogenation. The (fluoroalkyl)benzyl alcohols can be converted to corresponding (fluoroalkyl)benzyl bromides by substitution reaction at hydroxyl group by using hydrogen bromide, etc.

The (fluoroalkyl)benzenecarboxylic acid chloride is produced by the reaction of the (fluoroalkyl)benzenecarboxylic acid fluoride after the halogen-fluorine exchange mentioned above with silicon tetrachloride, or the reaction of the purified (fluoroalkyl)benzenecarboxylic acid with phosphoryl chloride, thionyl chloride, phosphorus chloride, etc. In particular, the production of the acid chlorides from carboxylic acids are easy and various methods have been known. For example, the purified (fluoroalkyl)benzenecarboxylic acid is dissolved in acetonitrile, and then excess of thionyl chloride is added to the solution. The reaction is completed by maintaining the solution at a reflux temperature for several hours. The catalyst is usually not required, but zinc chloride, pyridine, triethylamine, etc. can be used as the catalyst. A high-purity (fluoroalkyl)benzenecarboxylic acid chloride is obtained by removing the solvent and excess thionyl chloride from the reaction product and then distilling by a distillation column. If the further removal of impurities is required, the distillation procedure is repeated, preferably in combination with molecular distillation.

The (fluoroalkyl)benzaldehyde can be produced by catalytically reducing the (fluoroalkyl)benzenecarboxylic acid chloride with hydrogen in a solvent such as xylene and toluene. The catalytic reduction of the (fluoroalkyl)benzenecarboxylic acid chloride is known as Rosenmund method. Although pool in duplicability in some cases, a successful result is obtained by adding quinoline-S (prepared from quinoline and sulfur) in the presence of a hydrogen chloride capturer such as amines and pyridine or a base such as sodium acetate. The catalyst for reduction is preferably palladium-carbon, etc. After the catalytic reduction, the reaction mixture is filtered to remove the catalyst and impurities and distilled preferably after washed with water, etc. Thus, according to the invention, impurity reduced (fluoroalkyl)benzaldehydes care produced. If the further removal of impurities is required, the distillation procedure is repeated, preferably in combination with molecular distillation.

The (fluoroalkyl)benzenecarboxylic acid ester is produced by the reaction of the (fluoroalkyl)benzenecarboxylic acid fluoride, which may be a crude product obtained by removing residual HF and HCl from the product of halogen-fluorine exchange or may be a purified product obtained by distilling the crude product, with alcohol such as methyl alcohol and ethyl alcohol. This reaction is a well known method for producing esters from acid halides, and may be conducted, for example, by dropping the product into excess methanol. HF generated during the reaction is preferably recovered by a partial condenser for reuse, or may be captured by a coexisting base such as pyridine and triethylamine. The reaction proceeds at room temperature, but is completed for several hours at elevated temperatures under heating. When the base is not used, the reaction is preferably conducted at the reflux temperature of methanol to promote the removal of HF being generated. A high-purity methyl (fluoroalkyl)benzenecarboxylate is obtained by removing the excess methanol from the reaction solution by distillation, removing impurities such as HF and base, if still remain, by a suitable method such as filtration and washing with water, and distilling the resultant product. If the further removal of impurities is required, the distillation procedure is repeated, preferably in combination with molecular distillation.

The (fluoroalkyl)benzenecarboxylamide is produced by the reaction of the (fluoroalkyl)benzenecarboxylic acid fluoride, which may be a crude product obtained by removing residual HF and HCl from the product of halogen-fluorine exchange or may be a purified product obtained by distilling the crude product, with ammonia, primary amine or secondary amine. This reaction is also a well known method for producing acid amides from acid halides similarly to the method for producing ester derivatives. The reaction is conducted, for example, by dropping the (fluoroalkyl)benzenecarboxylic acid fluoride into a liquid ammonia at arbitrary temperatures. To capture the generated HF, it is preferred to use ammonia excessively or to add a tertiary amine. When ammonia or low-boiling amines having a high vapor pressure are used, the reaction can be performed in the two-phase system of an aqueous ammonia solution and an organic solvent. In this reaction system, since the salt of HF enters into the aqueous phase, the burden of the purification in the subsequent step is reduced. After the reaction, the excess ammonia, etc., are removed by distillation and the impurities are removed by washing with water. Then, as in the case of the production of the (fluoroalkyl)benzenecarboxylic acids, a purified (fluoroalkyl)benzenecarboxylamide is obtained by crystallization from a solvent such as hexane. If the further removal of impurities is required, the above procedures are repeated.

The (fluoroalkyl)benzenecarboxylamides can be converted into (fluoroalkyl)benzonitriles by dehydration using a dehydrating agent. This reaction is a well known method for conversion of primary amides into nitriles, and a dehydrating agent such as phosphorus pentoxide, phosphorus pentachloride and thionyl chloride is usable, Alternatively, the (fluoroalkyl)benzonitriles can be produced also by the dehydration in the presence of ammonia of the starting (fluoroalkyl)benzenecarboxylic acids in the presence of methanesulfonamide and phosphorus pentachloride, or in the presence of p-toluenesulfonamide or urea together with a catalyst such as $H_3PO_4$. After removing the solvent, ammonia, etc., the obtained reaction product is distilled to obtain high-purity (fluoroalkyl)benzonitriles. If the further removal of impurities is required, the distillation procedure is repeated, preferably in combination with molecular distillation.

As described above, the present invention makes it possible to reduce the residual amounts of halogens and metals of the (fluoroalkyl)benzene derivatives even when they are produced by the photohalogenation and the halogen-fluorine exchange which are simple but involve a problem of residual impurities such as halogens, thereby enabling the production of high-purity fluoroalkyl compounds which are useful as intermediates for the production of functional chemical products such as medicines and electronic materials.

The present invention will be described in more detail by reference to the following examples, reference example and comparative examples, but it should be noted that the examples are not intended to limit the invention thereto.

REFERENCE EXAMPLE

Production of 3,5-dimethylbenzoyl chloride

Method A

Into a 1-L three-necked flask equipped with a nitrogen gas inlet and a reflux condenser, were charged 300 g (2 mol) of 3,5-dimethylbenzoic acid, 391 g (2 mol) of (trichloromethyl)benzene and 0.28 g (0.0017 mol) of iron (III) chloride as a catalyst. The reaction solution was heated to 60° C. while stirring under a nitrogen flow and maintained there for 30 min. The reaction was allowed to further proceed at 130° C. for 130 min. During the reaction, hydrogen chloride generated was washed away and captured by an aqueous alkali solution. The result of gas chromatographic analysis of the reaction product solution showed the production of 324 g (1.92 mol) of the aimed 3,5-dimethylbenzoyl chloride (yield: 96%). By vacuum distillation, 292.7 g (1.74 mol) of 3,5-dimethylbenzoyl chloride was isolated (yield: 87%).

Method B

Into the same apparatus as used in the method A, were charged 300 g (2 mol) of 3,5-dimethylbenzoic acid and 357.2 g (3 mol) of thionyl chloride. The temperature was raised to 80° C. while stirring in a nitrogen atmosphere to allow the reaction to proceed for 3 h under reflux. During the reaction, sulfur dioxide and hydrogen chloride generated were washed away and captured by an aqueous alkali solution, The result of analysis of the reaction product solution showed the production of 310 g (1.84 mol) of the aimed 3,5-dimethylbenzoyl chloride (yield: 92%). By vacuum distillation, 287-(1.7 mol) of 3,5-dimethylbenzoyl chloride was isolated (yield: 85%).

Method C

Into a 2-L three-necked flask equipped with a gas blowing tube, a reflux condenser and a stirrer, were charged 269.7 g (2 mol) of 3,5-dimehtylbenzaldehyde and 800 g of o-dichlorobenzene. The temperature of the reaction system was controlled to 5° C. while introducing a nitrogen gas. After bubbling the reaction solution by blowing a nitrogen gas for one hour, the feed of nitrogen was stopped and the feed of chlorine was started. Simultaneously with the feed of chlorine, the irradiation of light from a mercury lamp was started. The photochlorination was completed after 6 h. The quantitative analysis by gas chromatography showed the production of 1.4 mol of 3,5-dimethylbenzoyl chloride (yield: 70%). By vacuum distillation, 236 g (1.4 mol) of 3,5-dimethylbenzoyl chloride was isolated (yield: 68%). The results of total elements analysis by ICP showed that a total content of residual group 3 to group 12 metals was 500 ppm or lower in which the highest was 10 ppm of Fe and the second highest was 30 ppm of Zn.

EXAMPLE 1

Production of 3,5-bis(trifluoromethyl)benzoic acid (1) Production of 3,5-bis(trichloromethyl)benzoyl chloride A 500-mL four-necked flask equipped with a tube for receiving a high-pressure mercury lamp, a chlorine gas blowing tube and a reflux condenser was changed with 250 g of 3,5-dimethylbenzoyl chloride obtained by the method A of Reference Example and the temperature was raised under nitrogen flow. When the inner temperature reached 140° C., nitrogen was changed to chlorine gas, and simultaneously, the photochlorination of branched methyl group was started by the irradiation of light from the mercury lamp. The reaction solution was analyzed by gas chromatography at regular intervals, and the reaction was continued until only the peak attributable to the aimed 3,5-bis(trichloromethyl)benzoyl chloride was observed. The time required for completing the photochlorination reaction was 22 h, during which 729.1 g of chlorine (1.2 times the stoichiometric amount) was supplied. The conversion of 3,5-dimethylbenzoyl chloride was 100% and the yield of 3,5-bis(trichloromethyl)benzoyl chloride was 95%.

By collecting a main fraction of 146-147° C./3 mmHg by vacuum distillation, 517.5 g of 3,5-bis(trichloromethyl)benzoyl chloride was obtained (yield: 93%). The results of ICP analysis showed that the distillation-purified 3,5-bis(trichloromethyl)benzoyl chloride contained Ti, Zr, V, Nb, Cr, Mo, W, Mn, Fe, Ru, Co, Rh and Ni in an amount of 10 ppm or lower for each.

(2) Production of 3,5-bis(trifluoromethyl)benzoyl fluoride

A 300-mL Hastelloy C autoclave equipped with a reflux condenser was charged with 50 g (0.133 mol) of the 3,5-bis (trichloromethyl)benzoyl chloride prepared above. After replacing the inner atmosphere of the autoclave by nitrogen, 80 g (4 mol) of anhydrous hydrogen fluoride (HF) was introduced. The contents were heated to 150° C. under stirring to proceed the reaction by maintaining the temperature for 13 h. As the reaction proceeded, the inner pressure of the autoclave became higher than the vapor pressure of HF because of the generation of hydrogen chloride. Therefore, the inner pressure was maintained at 3 MPa by purging the generated hydrogen chloride through a valve disposed downstream the reflux condenser. When the pressure rise was almost not noticed, the autoclave was cooled to terminate the reaction.

After removing the unreacted hydrogen fluoride and residual hydrogen chloride by suction under reduce pressure, the reaction product solution in the autoclave was transferred into a closed container kept under nitrogen atmosphere. A portion of the reaction product solution was sampled and analyzed by gas chromatography. The result showed that the aimed product, i.e., 3,5-bis(trifluoromethyl)benzoyl fluoride resulted from the complete replacement of chlorines with fluorines is produced in an amount of 0.11 mol (yield: 83%). The purity determined by gas chromatography was 99.8%. The residual chlorine content estimated from the purity was 1% by weight or lower.

(3) Production of 3,5-bis(trifluoromethyl)benzoic acid

The crude 3,5-bis(trifluoromethyl)benzoyl fluoride as prepared above was added to a mixed solvent of 100 g of ether and 100 g of ice water. By mixing, 3,5-bis(trifluoromethyl) benzoyl fluoride was gradually hydrolyzed into 3,5-bis(trifluoromethyl)benzoic acid with evolution of heat. By removing the ether solvent by distillation under reduced pressure, 0.11 mol of crude 3,5-bis(trifluoromethyl)benzoic acid was obtained. Then, the crude 3,5-bis(trifluoromethyl)benzoic acid was dissolved in hexane at its reflux temperature, filtered while being hot, and then crystallized at 0° C. to obtain acicular crystals of 3,5-bis(trifluoromethyl)benzoic acid. The yielded amount was 0.094 mol (recovery: 85%).

The purity of crystals determined lay gas chromatography was 99.9% or higher. As a result of quantitative analysis using an oxyhydrogen flame combustion apparatus, the total content of impurity chlorine in the crystals was 500 ppm. The content of ionic chlorine was 50 ppm when determined by dissolving the crystals in diethyl ether and extracting the solution with water. The total elements analysis by ICP showed that none of Li, Na, K, Mg, Ca, Sr, Ba, Sc, Y, Ti, Zr, If, Nb, Cr, Mo, W, Mn, Fe, Ru, Co, Rh, Ni, Pd, Pt, Cu, Ag, Au, Zn, Cd, Al, In, Si, Sn, Pb, P, Sb and S were detected. The lower detection limits of the total elements analysis by ICP apparatus were 100 ppm for In and Sb; 50 ppm for Li, K, Pt, Pb and P; 20 ppm for Ti, W, Mo and Al; and 1 to 10 ppm or lower for other elements. The IPC quantitative analysis was separately repeated on group 1 and group 2 elements by increasing the accuracy of measurement. The content was 10 ppm or less for each case.

EXAMPLE 2

Production of 3,5-bis(trifluoromethyl)benzoic acid 3,5-Bis(trifluoromethyl)benzoyl fluoride (28 g) obtained after completion of the chlorine-fluorine exchange using HF in Example 1 was distilled to collect 22.5 g of a 78-83° C./50 mmHg fraction. Subsequently, the fraction was treated in the same manner as in Example 1 to obtain 20 g (0.08 mol) of acicular crystals of 3,5-bis(trifluoromethyl)benzoic acid.

The purity of the product determined by gas chromatography was 99.9% or higher, and the total content of impurity chlorine remained was 50 ppm or lower. The total elements analysis by ICP showed that none of Li, Na, K, Mg, Ca, Sr, Ba, Sc, Y, Ti, Zr, V, Tb, Cr, Mo, W, Mn, Fe, Ru, Co, Rh, Ni, Pd, Pt, Cu, Ag, Au, Zn, Cd, Al, In, Si, Sn, Pb, P, Sb and S were detected. The content determined by the ICP quantitative analysis was 10 ppm or lower for each of group 1 and group 2 elements.

EXAMPLE 3

Production of 3,5-bis(trifluoromethyl)benzoyl chloride

By distilling 280 g of 3,5-bis(trifluoromethyl)benzoyl fluoride obtained after the chlorine-fluorine exchange using HF in the same manner as in Example 1, 225 g of a 78-83° C./60 mmHg fraction was collected. After adding 5 g of aluminum chloride, the fraction was maintained at 40° C. Then, after adding 49 g of silicon tetrachloride over 2 h, the reaction was further continued for 2' h. The reaction product mixture was mixed with molecular sieves, filtered and then supplied to a distillation column in which benzene was refluxed, thereby removing low-boiling components. The bottom liquid of the distillation column was filtered and then distilled under a reduced pressure of 11 mmHg to collect 156 g of a 69-70° C. fraction. The obtained product was identified as the aimed 3,5-bis(trifluoromethyl)benzoyl chloride by NMR analysis. The purity determined by gas chromatography was 99.9% or higher. The results of ICP total elements analysis showed that none of Li, Na, K, Mg, Ca, Sr, Ba, Sc, Y, Ti, Zr, V, Nb, Cr, Mo, W, Mn, Fe, Ru, Co, Rh, Ni, Pd, Pt, Cu, Ag, Au, Zn, Cd, Al, In, Si, Sn, Pb, P, Sb and S were detected, and the content of each of group 1 and group 2 elements was 1 ppm or lower.

EXAMPLE 4

Production of methyl 3,5-bis(trifluoromethyl)benzoate

Into 25.9 g (0.8 mol) of methanol, 13.8 g (0.053 mol) of the fraction of 3,5-bis(trifluoromethyl)benzoyl fluoride obtained after the chlorine-fluorine exchange using HF in the same manner as in Example 2 was added dropwise over 60 min. Then, the reaction was allowed to proceed at 40° C. for 4 h. By gas chromatographic analysis, the production of 14.2 g (0.052 mol) of the aimed methyl 3,5-bis(trifluoromethyl)benzoate was confirmed (yield: 98%, selectivity: 100%). By vacuum distillation, 13.9 g (0.05 mol) of methyl 3,5-bis(trifluoromethyl)benzoate was isolated (yield: 96%). The purity determined by gas chromatography was 99% or higher. The results of ICP total elements analysis showed that none of Li, Na, K, Mg, Ca, Sr, Ba, Sc, Y, Ti, Zr, V, Nb, Cr, Mo, W, Mn, Fe, Ru, Co, Rh, Ni, Pd, Pt, Cu, Ag, Au, Zn, Cd, Al, In, Si, Sn, Pb, P, Sb and S were detected, and the content of each of group 1 and group 2 elements was 1 ppm or lower.

EXAMPLE 5

Production of 3,5-bis(trifluoromethyl)benzaldehyde

Into a 1-L autoclave, were charged 100 g (0.36 mob) of 3,5-bis(trifluoromethyl)benzoyl chloride produced in the same manner as in Example 3, 350 g of dry toluene, 90 g (1.08 mol) of anhydrous sodium acetate and 10.9 g 10% palladium-carbon. After adding 21.7 g (0.17 mol) of quinoline and 3.6 g (0.11 mol) of sulfur, the contents were refluxed under heating for 5 h. Then, quinoline-S diluted by dry xylene to 250 ml was added. After evacuating the autoclave, the inner pressure was adjusted to 1 MPa by introducing hydrogen. While successively supplying hydrogen to maintain the inner pressure at 1 MPa, the contents were stirred at room temperature for one hour. The temperature was raised to 50° C. and the stirring was continued for 2 h. Then, the temperature was returned to room temperature and the stirring was continued for 24 h to complete the reaction. After returning the inner pressure to atmospheric pressure, the reaction product solution was filtered and then washed with toluene. The filtrate was successively washed with a 5% sodium carbonate aqueous solution and water, and then dried over anhydrous sodium sulfate. After removing anhydrous sodium sulfate by filtration and toluene by distillation, the obtained product was analyzed by gas chromatography.

It was confirmed that 65.4 g (0.27 mol) of the aimed 3,5-bis(trifluoromethyl)benzaldehyde was produced (yield: 76%). By vacuum distillation, 63.0 g (0.27 mol) of 3,5-bis(trifluoromethyl)benzaldehyde was isolated (yield: 72%). The purity determined by gas chromatography was 99% E) or higher. The results of ICP total elements analysis showed that none of Li, Na, K, Mg, Ca, Sr, Ba, Sc, Y, Ti, Zr, V, Nb, Cr, Mo, W, Mn, Fe, Ru, Co, Rh, Ni, Pd, Pt, Cu, Ag, Au, Zn, Cd, Al, In, Si, Sn, Pb, P, Sb and S were detected, and the content of each of group 1 and group 2 elements was 1 ppm or lower.

EXAMPLE 6

Production of 3,5-bis(trifluoromethyl)phenol (1) Production of 3,5-bis(trifluoromethyl)acetophenone A mixture of 9.0 g (0.0345 mol) of 3,5-bis(trifluoromethyl)benzoyl fluoride obtained in the same manner as in Example 2 and 16 mL of HMPA Was stirred at room temperature for 30 min. After mixing 5 mL (0.0361 mol) of tetramethyltin and 14 mg (0.018 mol) of a palladium-phosphine catalyst (PhCH$_2$Pd(PPh$_3$)$_2$Cl), the temperature was raised to 65° C. After stirring for one hour, the temperature was lowered to room temperature and 20 mL of water was mixed to separate an organic phase. After extracting the aqueous phase with 10 mL of diethyl ether, the collected organic solvent phase was washed four times with each 20 mL of water. After dried over magnesium sulfate, the organic phase was analyzed by gas chromatography. It was confirmed that 7.25 g (0.0283 mol) of the aimed 3,5-bis(trifluoromethyl)acetophenone was produced (yield: 82%). By vacuum distillation, 3,5-bis(trifluoromethyl)acetophenone was isolated (yield: 77%).

(2) Production of 3,5-bis(trifluoromethyl)phenol

A mixture of 100 g (0.39 mol) of 3,5-bis(trifluoromethyl)acetophenone obtained above, 155.2 g of (0.74 mol) of trifluoroacetic anhydride and 400 ml of chloroform was stirred it 0° C. in a nitrogen atmosphere. After adding 19.7 g (0.52 mol) of a 90% hydrogen peroxide aqueous solution from a dropping funnel over 30 min and stirring the mixture for one our, the temperature was raised to 70° C. to proceed the reaction for 5 h. After completion of the reaction, the temperature was returned to room temperature. The reaction product solution was poured into a separating funnel containing a saturated brine and washed with water. The organic phase separated was analyzed by gas chromatography. It was confirmed that 57.5 g (0.25 mol) of the aimed 3,5-bis(trifluoromethyl)phenol was produced (yield; 67%). By vacuum distillation, 53.3 g (0.23 mol) of 3,5-bis(trifluoromethyl)phenol was isolated (yield: 63%). The purity determined by gas chromatography was 99% or higher. The results of ICP total elements analysis showed that none of Li, Na, K, Mg, Ca, Sr, Ba, Sc, Er, Ti, Zr, V, Nb, Cr, Mo, V, Mn, Fe, Ru, Co, Rh, Ni, Pd, Pt, Cu, Ag, Au, Zn, Cd, Al, In, Si, Sn, Pb, P, Sb and S were detected, and the content of each of group 1 and group 2 elements was 1 ppm or lower.

EXAMPLE 7

Production of 3,5-bis(trifluoromethyl)benzamide

Into a three-necked flask containing 65.5 ml (3.8 mol) of ice-cooled aqueous ammonia and 300 g of toluene, was added dropwise 100 g (0.38 mol) of 3,5-bis(trifluoromethyl)benzoyl fluoride obtained in the same manner as in Example 2 over one hour. After the dropwise addition, the temperature was adjusted to 30° C. to initiate the reaction. The reaction was continued for 5 h. The results of gas chromatographic analysis of the toluene phase showed that 93.8 g (0.38 mol) of the aimed 3,5-bis(trifluoromethyl)benzamide was produced (yield: 98%; selectivity: 100%). By the crystallization in the same manner as in Example 2, 93.9 g (0.37 mol) of 3,5-bis(trifluoromethyl)benzamide was isolated (yield: 95%). The purity determined by gas chromatography was 99% or higher. The results of ICP total elements analysis showed that none of Li, Na, K, Mg, Ca, Sr, Ba, Sc, Y, Ti, Zr, V, Nb, Cr, Mo, W, Mn, Fe, Ru, Co, Rh, Ni, Pd, Pt, Cu, Ag, Au. Zn, Cd, Al, In, Si, Sn, Pb, P, Sb and S were detected, and the content of each of group 1 and group 2 elements was 1 ppm or lower.

EXAMPLE 8

Production of 3,5-bis(trifluoromethyl)benzonitrile

Into a 2-L three-necked flask, were charged 300 g (1.17 mol) of 3,5-bis(trifluoromethyl)benzamide obtained in the same manner as in Example 7, 183.6 g (0.7 mol) of triphenylphosphine, 107.7 g (0.7 mol) of carbon tetrachloride and 400 ml of tetrahydrofuran. The liquid mixture was heated to 60° C. under stirring to proceed the reaction for 180 min. After adding 6 g (0.04 mmol) of phosphorus pentoxide, a distillation apparatus was fitted to the flask to collect 237.1 g of a 155° C. fraction by the distillation under atmospheric pressure. The results of analyzing the fraction by gas chromatography showed that 0.99 mol of the aimed 3,5-bis(trifluoromethyl)benzonitrile having a purity of 99.8% was produced (yield: 85%). The results of ICP total elements analysis showed that none of Li, Na, K, Mg, Ca, Sr, Ba, Sc, Y, Ti, Zr, V, Nb, Cr, Mo, W, Mn, Fe, Ru, Co, Rh, Ni, Pd, Pt, Cu, Ag, Au, Zn, Cd, Al, In, Si, Sn, Pb, P, Sb and S were detected, and the content of each of group 1 and group 2 elements was 1 ppm or lower.

EXAMPLE 9

Production of 3,5-bis(trifluoromethyl)benzyl alcohol

Into 460 ml (0.46 mol) of a 1.0 M diethyl ether solution of aluminum lithium hydride cooled to 0° C. 80 g (0.31 mol) of 3,5-bis(trifluoromethylbenzoic acid obtained in the same manner as in Example 2 was gradually added. The reaction solution was heated to the reflux temperature (35° C.) while stirring under a nitrogen flow to continue the reaction for 10 h. After completion of the reaction, the reaction solution was cooled to 0° C. and 20 ml of water was added over 15 min. Then, 20 ml of a 15% sodium hydroxide aqueous solution and 60 ml of water were gradually added. After stirring for 30 min, the organic phase was separated by filtration and dried over anhydrous sodium sulfate. After removing anhydrous sodium sulfate by filtration, the organic phase was analyzed by gas chromatography. It was confirmed that 58.6 g (0.24 mol) of the aimed 3,5-bis(trifluoromethyl)benzyl alcohol was produced (yield: 78%; selectivity: 91%). By vacuum distillation after removing ether, 55.9 g (0.23 mol) of 3,5-bis(trifluoromethyl)benzyl alcohol was isolated (yield: 74%). The purity determined by gas chromatography was 99% or higher. The results of ICP total elements analysis showed that none of Li, Na, K, Mg, Ca, Sr, Ba, Sc, Y, Ti, Zr, V, Nb, Cr, Mc, W, Mn, Fe, Ru, Co, Rh, Ni, Pd, Pt, Cu, Ag, Au, Zn, Cd, Al, In, Si, Sn, Pb, P, Sb and S were detected, and the content of each of group 1 and group 2 elements was 1 ppm or lower.

EXAMPLE 10

Production of 3,5-bis(trifluoromethyl)benzylamine

Into a 300-mL autoclave, were charged 145.3 g (0.60 mol) of 3,5-bis(trifluoromethyl)bonzaldehyde obtained in the same manner as in Example 5, 60 mL of a cooled ethanol solution containing 10.3 g (0.60 mol) of liquid ammonia and 2 g of Raney nickel. The mixture was heated to 40° C. while stirring under a hydrogen pressure (9 MPa) to proceed the reaction for one hour. The reaction was continued at 70° C. for 30 min and then the reaction product solution was discharged. After removing the catalyst by filtration, the reaction Solution was analyzed by gas chromatography. It was confirmed that 128.9 g (0.53 mol) of the aimed 3,5-bis(trifluoromethyl)benzylamine was produced (yield: 89%; selectivity: 93%). By vacuum distillation, 124.0 g (0.51 mol) of 3,5-bis(trifluoromethyl)benzylamine was isolated (yield: 85%). The purity determined by gas chromatography was 99% or higher. The results of ICP total elements analysis showed that none of Li, Na, K, Mg, Ca, Sr, Ba, Sc, Y, Ti, Zr, V, Nb, Cr, Mo, W, Mn, Fe, Ru, Co, Rh, Ni, Pd, Pt, Cu, Ag, Au, Zn, Cd, Al, In, Si, Sn, Pb, P, Sb and S were detected, and the content of each of group 1 and group 2 elements was 1 ppm or lower.

EXAMPLE 11

Production of m-(triflouromethyl)benzoyl fluoride

The procedure of Example 2 was repeated except for using m-(trichloromethyl)benzoyl chloride as the starting compound instead of 3,5-bis(trichloromethyl)benzoyl chloride. The yield and selectivity of the aimed m-(trifluoromethyl)benzoyl fluoride were 92% and 98%, respectively. The purity determined by gas chromatography was 99% or higher. The results of ICP total elements analysis showed that none of Li, Na, K, Mg, Ca, Sr, Ba, Sc, Y, Ti, Zr, V, Nb, Cr, Mo, W, Mn, Fe, Ru, Co, Ph, Ni, Pd, Pt, Cu, Ag, Au, Zn, Cd, Al, In, Si, Sn, Pb, P, Sb and S were detected, and the content of each of group 1 and group 2 elements was 1 ppm or lower.

COMPARATIVE EXAMPLE 1

The procedure of Example 1 was repeated except for using 3,5-dimethylbenzyl chloride containing 570 ppm of Fe, 220 ppm of Zn and 130 ppm of Sn. The yield of the chloride after the photochlorination was 86%, whereas 95% in Example 1. The purity of 3,5-bis(trifluoromethyl)benzoyl fluoride obtained by HF exchange reaction was 89%, and the residual of total impurity chlorine was 2.3% by weight.

COMPARATIVE EXAMPLE 2

In the fluorine exchange reaction using HF, the procedure of Example 1 was repeated except for using HF 8 times the substrate by mole. Although the yield of the chloride after the photochlorination was 94.8%, the purity of 3,5-bis(triflouromethyl)benzoyl fluoride was 12% and the residual of total chlorine was 12.6% by weight after the HF exchange reaction,

COMPARATIVE EXAMPLE 3

The procedure of Example 1 was repeated except that the temperature and time of the fluorine exchange using HF were changed to 130° C. and 5 h. The yield and selectivity of 3,5-bis(trifluoromethyl)benzoyl fluoride were 28% and 41%, respectively. The purity of 3,5-bis(trifluoromethyl)benzoyl fluoride was 58%.

COMPARATIVE EXAMPLE 4

The procedure of Comparative Example 3 was repeated except for changing the reaction temperature and reaction time to 100° C. and 45 h. The yield and selectivity of 3,5-bis(trifluoromethyl)benzoyl fluoride were 49% and 58%, respectively.

COMPARATIVE EXAMPLE 5

The procedure of Example 1 was repeated except for changing the charging molar ratio of HF to 20 times, the reaction temperature to 130° C. and the reaction time to 12 h. The yield and selectivity of 3,5-bis(trifluoromethyl)benzoyl fluoride were 2.9% and 4.2%, respectively.

COMPARATIVE EXAMPLE 6

The procedure of Comparative Example 5 was repeated except for changing the charging molar ratio of HF to 30 times. The yield and selectivity of 3,5-bis(trifluoromethyl)benzoyl fluoride were 69% and 89%, respectively.

COMPARATIVE EXAMPLE 7

The procedure of Comparative Example 5 was repeated except for changing the charging molar ratio of HF to 40 times. The yield and selectivity of 3,5-bis(trifluoromethyl)benzoyl fluoride were 70% and 90%, respectively.

COMPARATIVE EXAMPLE 8

The procedure of Example 4 was repeated except for changing the reaction temperature to 130° C. and the molar ratio of HF to 8. The yield of methyl 3,5-bis(trifluoromethyl)benzoate was 3.4% and the residual of the total chlorine was 3.1% by weight.

In the following Table 1, the results of Examples 1 to 4 and Comparative Examples 1 to 8 are compared.

TABLE 1

| | Photohalogenation | | | | | Fluorine exchange | | | |
|---|---|---|---|---|---|---|---|---|---|
| | Residual metal content in starting material (ppm) | | | | | HF/ substrate | | | |
| | total metals | Fe | Zn | Sn | Yield (%) | (molar ratio) | Temp. (° C.) | Time (h) | Yield (%) |
| Examples | | | | | | | | | |
| 1 | ≦500 | 110 | 30 | — | 95 | 30 | 150 | 13 | 85 |
| 2 | ≦500 | * | * | * | 96 | 30 | 150 | 13 | 86 |
| 3 | ≦500 | * | * | * | 94.6 | 30 | 150 | 13 | 87 |
| 4 | ≦500 | * | * | * | 95.3 | 30 | 150 | 13 | 85 |
| Comparative Examples | | | | | | | | | |
| 1 | ca. 1000 | 570 | 220 | 130 | 86 | 30 | 150 | 13 | 86 |
| 2 | ≦500 | 110 | 30 | — | 94.8 | 8 | 150 | 13 | |
| 3 | ≦500 | 110 | 30 | — | 94.6 | 30 | 130 | 13 | 28 |
| 4 | ≦500 | 110 | 30 | — | 95.1 | 30 | 100 | 13 | 49 |
| 5 | ≦500 | 110 | 30 | — | 95.2 | 20 | 130 | 13 | 2.9 |
| 6 | ≦500 | 110 | 30 | — | 94.9 | 30 | 130 | 13 | 69 |
| 7 | ≦500 | 110 | 30 | — | 94.8 | 40 | 130 | 13 | 70 |
| 8 | ≦500 | 110 | 30 | — | 94.8 | 8 | 150 | 13 | 70 |

| | | Impurities in final product | | |
|---|---|---|---|---|
| | Final product | Purity (%) | Residual chlorine | Residual metal |
| Examples | | | | |
| 1 | 3,5-bis(trifluoromethyl)benzoic acid | 99.8 | ≦500 ppm | Not detected |
| 2 | 3,5-bis(trifluoromethyl)benzoic acid | 99.8 | ≦50 ppm | Not detected |
| 3 | 3,5-bis(trifluoromethyl)benzoyl chloride | 99.9 | ≦50 ppm | Not detected |
| 4 | methyl 3,5-bis(trifluoromethyl)benzoate | 99.9 | ≦50 ppm | Not detected |
| Comparative Examples | | | | |
| 1 | 3,5-bis(trifluoromethyl)benzoic acid | 89 | 2.3 wt % | Detected |
| 2 | 3,5-bis(trifluoromethyl)benzoic acid | 12 | 12.6 wt % | Detected |
| 3 | 3,5-bis(trifluoromethyl)benzoic acid | 58 | 1.8 wt % | Detected |
| 4 | 3,5-bis(trifluoromethyl)fluoride | 57 | 12.3 wt % | Detected |
| 5 | 3,5-bis(trifluoromethyl)fluoride | — | — | Detected |
| 6 | 3,5-bis(trifluoromethyl)fluoride | — | 8.8 wt % | Detected |

TABLE 1-continued

| | | | | |
|---|---|---|---|---|
| 7 | 3,5-bis(trifluoromethyl)fluoride | 66 | 4.8 wt % | Detected |
| 8 | methyl 3,5-bis(trifluoromethyl)benzoate | 78 | 1.8 wt % | Detected |

Note
* Product of the fluorine exchange was distilled.

EXAMPLE 12

3-(Trifluoromethyl)benzoic acid

The procedure of Example 1 was repeated except for using 3-trichloromethyl)benzoyl chloride as the starting material instead of 3,5-bis(trichloromethyl)benzoyl chloride. The yield and selectivity of the aimed 3-(trifluoromethyl)benzoic acid were 92% and 98%, respectively.

EXAMPLE 13

4-(Trifluoromethyl)benzoic acid

The procedure of Example 1 was repeated except for using 4-(trichloromethyl)benzoyl chloride as the starting material instead of 3,5-bis(trichloromethyl)benzoyl chloride. The yield of the aimed 4-(trifluoromethyl)benzoic acid was 93%.

EXAMPLE 14

2,4-Bis(trifluoromethyl)benzoic acid

The procedure of Example 1 was repeated except for using 2,4-bis(trichloromethyl)benzoyl chloride as the starting material instead of 3,5-bis(trichloromethyl)benzoyl chloride. The yield and selectivity of the aimed 2,4-bis(trifluoromethyl)benzoic acid were 87% and 97%, respectively.

EXAMPLE 15

3,4-Bis(trifluoromethyl)benzoic acid

The procedure of Example 1 was repeated except for using 3,4-bis(trichloromethyl)benzoyl chloride as the starting material instead of 3,5-bis(trichloromethyl)benzoyl chloride. The yield and selectivity of the aimed 3,4-bis(trifluoromethyl)benzoic acid were 88% and 98%, respectively.

EXAMPLE 16

4-Trifluoromethylbiphenylcarboxylic acid

The procedure of Example 1 was repeated except for using 4-trichloromethylbiphenylcarboxylic acid chloride as the starting material instead of 3,5-bis(trichloromethyl)benzoyl chloride. The yield and selectivity of the aimed 4-trifluoromethylbiphenylcarboxylic acid were 90% and 96%, respectively.

EXAMPLES 17 TO 31

In the same manner as in Examples 2 to 16, each (fluoroalkyl)benzene derivative was produced. To reduce the impurities, the crystallization was conducted twice in Example 17 and the final distillation was repeated in the other examples. The purity, residual halogen content and residual metal content of the (fluoroalkyl)benzene derivatives are collectively shown in Table 2.

TABLE 2

| | Final product | Purity (%) | Residual chlorine (ppm) | Residual metal |
|---|---|---|---|---|
| Examples | | | | |
| 17 | 3,5-bis(trifluoromethyl)benzoic acid | ≧99.9 | ≦10 | Not detected |
| 18 | 3,5-bis(trifluoromethyl)benzoyl chloride | ≧99.9 | ≦10 | Not detected |
| 19 | methyl 3,5-bis(trifluoromethyl)benzoate | ≧99.9 | ≦10 | Not detected |
| 20 | 3,5-bis(trifluoromethyl)benzaldehyde | ≧99.9 | ≦10 | Not detected |
| 21 | 3,5-bis(trifluoromethyl)phenol | ≧99.9 | ≦10 | Not detected |
| 22 | 3,5-bis(trifluoromethyl)benzamide | ≧99.9 | ≦10 | Not detected |
| 23 | 3,5-bis(trifluoromethyl)benzonitrile | ≧99.9 | ≦10 | Not detected |
| 24 | 3,5-bis(trifluoromethyl)benzyl alcohol | ≧99.9 | ≦10 | Not detected |
| 25 | 3,5-bis(trifluoromethyl)benzylamine | ≧99.9 | ≦10 | Not detected |
| 26 | 3-trifluoromethylbenzoyl fluoride | ≧99.9 | ≦10 | Not detected |
| 27 | 3-trifluoromethylbenzoic acid | ≧99.9 | ≦10 | Not detected |
| 28 | 4-trifluoromethylbenzoic acid | ≧99.9 | ≦10 | Not detected |
| 29 | 2,4-bis(trifluoromethyl)benzoic acid | ≧99.9 | ≦10 | Not detected |
| 30 | 3,4-bis(trifluoromethyl)benzoic acid | ≧99.9 | ≦10 | Not detected |
| 31 | 4-trifluoromethylbiphenylcarboxylic acid | ≧99.9 | ≦10 | Not detected |

Residual metals: Li, Na, K, Mg, Ca, Sr, Ba, Sc, Y, Ti, Zr, V, Nb, Cr, Mo, W, Mn, Fe, Ru, Co, Rh, Ni, Pd, Pt, Cu, Ag, Au, Zn, Cd, Al, In, Si, Sn, Pb, P, Sb, S

COMPARATIVE EXAMPLES 9 TO 23

In the same manner as in Examples 17 to 31 except for changing the molar ratio of HF for the halogen-fluorine exchange to 8, each (fluoroalkyl)benzene derivative was produced. Any of the produced (fluoroalkyl)benzene derivatives contained residual metals in an amount of at least 50 ppm. The residual chlorine content was 1.1% by weight in minimum.

The purity of the (fluoroalkyl)benzene derivatives was only 62% at best.

INDUSTRIAL APPLICABILITY

In the known halogen-fluorine exchange for the production of (fluoroalkyl)benzene derivatives, it has been difficult to reduce the halogen impurity. The invention provides a method for producing (fluoroalkyl)benzene derivatives with reduced impurities such as halogens, which are useful as intermediates for functional chemical products such as medicines and electronic materials.

What is claimed is:

1. A process for producing a (fluoroalkyl)benzene derivative comprising:

a step of reducing a total content of group 3 to group 12 transition metals in an alkylbenzene derivative to 500 ppm or less on atomic basis, said alkylbenzene derivative being represented by the formula (1):

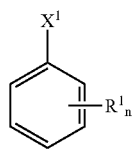

(1)

wherein $X^1$ is hydrogen, hydroxyl, alkyl, aryl, halogen inclusive of fluorine, formyl, carboxyl, nitro, cyano, amino, hydroxymethyl, aminomethyl, carbamoyl, sulfonic acid group or halogenocarbonyl inclusive of fluorocarbonyl, or $X^1$ is alkyloxycarbonyl, alkylcarbonyl, arylcarbonyl, alkyloxy or aryloxy, each being optionally substituted; $R^1$ is carboxyl, halogenocarbonyl inclusive of fluorocarbonyl, alkyloxycarbonyl, aryloxycarbonyl, substituted or unsubstituted alkyl, or substituted or unsubstituted aryl; n is an integer of 1 to 5 with the proviso that when n is 2 to 5, a plurality of $R^1$ groups may be the same or different, but at least one of $R^1$ is alkyl;

a step of halogenating said at least one alkyl group of the purified alkylbenzene derivative by a photohalogenation using a halogen other than fluorine to obtain a (haloalkyl)benzene derivative; and a step of subjecting the (haloalkyl)benzene derivative to a halogen-fluorine exchange using HF in an amount of 10 mol or more per one mole of the (haloalkyl)benzene derivative, thereby producing said high-purity (fluoroalkyl)benzene derivative represented by the formula (2):

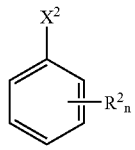

(2)

wherein $X^2$ corresponds to $X^1$ of the formula (1) and is hydrogen, hydroxyl, fluoroalkyl, aryl, halogen inclusive of fluorine, formyl, fluorocarbonyl, nitro, cyano, amino, hydroxyfluoromethyl, aminofluoromethyl, carbamoyl or sulfonylfluoride, or $X^1$ is fluoroalkyloxycarbonyl, fluoroalkylcarbonyl, arylcarbonyl, fluoroalkyloxy or aryloxy, each being optionally substituted; $R^2$ corresponds to $R^1$ of the formula (1) and is fluorocarbonyl, fluoroalkyloxycarbonyl, aryloxycarbonyl, substituted or unsubstituted fluoroalkyl, or substituted or unsubstituted aryl; n is an integer of 1 to 5 with the proviso that when n is 2 to 5, a plurality of $R^2$ groups may be the same or different, but at least one of $R^2$ is fluoroalkyl.

2. The process according to claim 1, wherein the photohalogenation is conducted by supplying chlorine, bromine or iodine in an amount of 50 to 3,000 parts by weight based on 100 parts by weight of the alkylbenzene derivative.

3. The process according to claim 1, wherein the photohalogenation is conducted at 50 to 250° C. under 0.05 to 0.5 MPa.

4. The process according to claim 1, wherein the halogen-fluorine exchange is conducted in the presence of an acid having a Hammett acidity function $H_0$ of −10 or less, or a Lewis acid selected from the group consisting of $BF_3$, $SbF_5$ and $TaF_5$.

5. The process according to claim 4, wherein the acid having a Hammett acidity function $H_0$ of −10 or less or the Lewis acid is used in an amount of 0.001 to 0.1 mol per one mole of HF.

6. The process according to claim 1, wherein the halogen-fluorine exchange is conducted at 20 to 400° C. for 0.1 to 20 h.

7. The process according to claim 2, wherein the photohalogenation is conducted at 50 to 250° C. under 0.05 to 0.5 MPa.

8. The process according to claim 2, wherein the halogen-fluorine exchange is conducted in the presence of an acid having a Hammett acidity function $H_0$ of −10 or less, or a Lewis acid selected from the group consisting of $BF_3$, $SbF_5$ and $TaF_5$.

9. The process according to claim 2, wherein the halogen-fluorine exchange is conducted at 20 to 400° C. for 0.1 to 20 h.

10. The process according to claim 3, wherein the halogen-fluorine exchange is conducted in the presence of an acid having a Hammett acidity function $H_0$ of −10 or less, or a Lewis acid selected from the group consisting of $BF_3$, $SbF_5$ and $TaF_5$.

* * * * *